United States Patent [19]
Hautmann

[11] Patent Number: 5,269,460
[45] Date of Patent: Dec. 14, 1993

[54] EVAPORATOR DEVICE, PARTICULARLY FOR VOLATILE ACTIVE SUBSTANCES SUCH AS INSECTICIDES, PERFUMES AND THE LIKE

[75] Inventor: Horst Hautmann, Neuburg, Fed. Rep. of Germany

[73] Assignee: Globol GmbH, Neuburg/Donau, Fed. Rep. of Germany

[21] Appl. No.: 911,222

[22] Filed: Jul. 9, 1992

[30] Foreign Application Priority Data

Aug. 21, 1991 [DE] Fed. Rep. of Germany ....... 4127692

[51] Int. Cl.$^5$ ..................... A01M 13/00; A01M 1/20; A61L 9/12
[52] U.S. Cl. ....................................... 239/35; 239/309
[58] Field of Search .................. 239/34, 35, 37, 43, 239/44, 49, 51.5, 57, 309, 326

[56] References Cited

U.S. PATENT DOCUMENTS

| | | | |
|---|---|---|---|
| 2,431,924 | 12/1947 | Dunaway | 239/35 |
| 4,161,284 | 7/1979 | Rattan | 239/43 |
| 4,293,095 | 10/1981 | Hamilton et al. | 239/35 |
| 4,339,079 | 7/1982 | Sato et al. | 239/43 |
| 4,526,320 | 7/1985 | von Philipp et al. | 239/43 |

FOREIGN PATENT DOCUMENTS

3212860A1 10/1982 Fed. Rep. of Germany .
2054435 4/1971 France .
2158356 11/1985 United Kingdom .

*Primary Examiner*—Andres Kashnikow
*Assistant Examiner*—Karen B. Merritt
*Attorney, Agent, or Firm*—Townsend and Townsend Khourie and Crew

[57] ABSTRACT

Disclosed is an evaporator for volatile active substances such as insecticides or perfumes. It has a housing containing ports through which the active substance emerges. The housing is made up of at least two housing sections which are movable about a hinge axis. At least one receiving section for an active substance container is provided and includes at least one opening device for opening the container. The operating condition is indicated, and there is a further container holding an indicator fluid which is opened when the evaporator is in use so that the indicator fluid can evaporate over the time period during which the active substance is depleted. A mounting member positions the indicator fluid container between the two housing sections, and one of the sections incorporates an opening behind which the indicator fluid container is positioned so that it can be viewed from the outside of the housing to determine the operating condition of the device, while the container holding the active substance cannot be viewed from the outside.

17 Claims, 4 Drawing Sheets

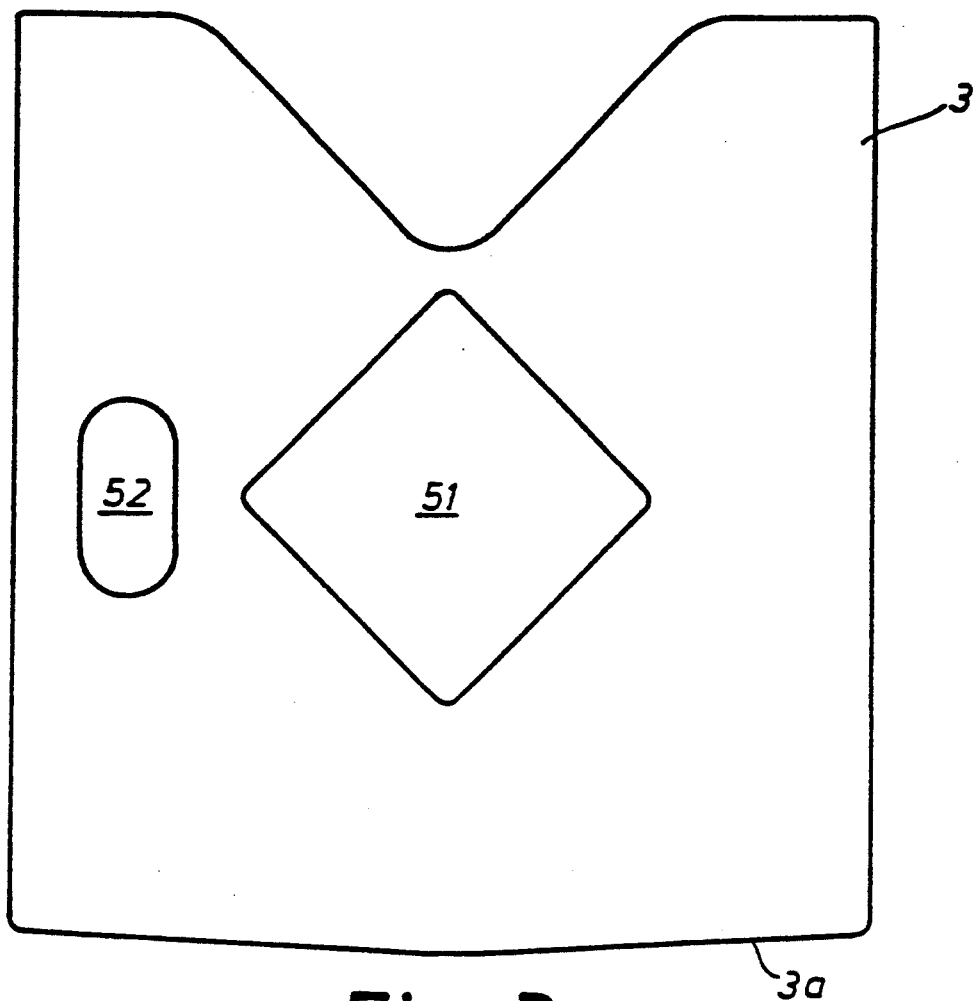
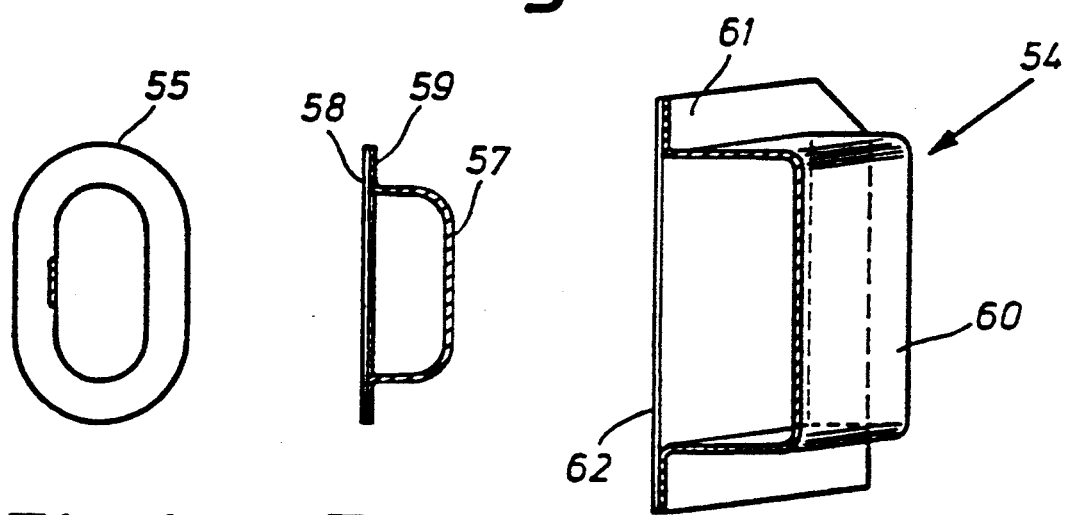

EVAPORATOR DEVICE, PARTICULARLY FOR VOLATILE ACTIVE SUBSTANCES SUCH AS INSECTICIDES, PERFUMES AND THE LIKE

BACKGROUND OF THE INVENTION

The invention relates to an evaporator device, particularly for a volatile substance such as an insecticide or a perfume.

An evaporator device of this type is known from EP 094 499, FIGS. 7 thru 9. A housing section contains an opener means acting in conjunction with a perforable container received in another housing section. The perforation of the container results from hinging its receiving housing section in the direction of the opener means. In this evaporator device the filling level of the container is not evident from the outside. The user is required to check the filling level by either noting the degree of evaporation of the evaporator device or to open the housing sections to inspect the container.

In a further embodiment of an evaporator device according to FIG. 1 of EP 094 499 the container receiving the active substances is disposed so that it is visible from the outside of the housing and, when the containers for the active substances are transparent, the filling level of the latter is evident from the outside.

In the described evaporator device the perforation of the container for receiving the active substances for the purpose of allowing the active substances to emerge is provided such that relatively small openings are incorporated in the perforated surface and that the active substances emerge from the container slowly.

SUMMARY OF THE INVENTION

The invention is based on the object of improving an evaporator device of the aforementioned kind so that high evaporation efficiency is ensured and so that the operating condition of the device is easily discernible.

This object is achieved according to the invention by means for indicating the operating condition.

The invention creates an evaporator device in which the active substance present in at least one container emerges practically completely following actuation of the evaporator device to permit an intensive evaporation of the active substance and in which a means for inspecting the operating condition is provided.

According to one preferred embodiment of the evaporator device a mounting member can be disposed in the housing in which the container(s) holding the active substance and a means for indicating the operating condition can be located.

In accordance with a preferred embodiment of the evaporator device the container receiving the active substance and the container serving as the means of indicating the operating condition preferably constitute a molded plastic part which is closed off by a perforable planar film or foil in that a circumferential edge or collar is formed by means of which each container can be mounted on the mounting member. Each container is assigned an opener means, the opener means for the container provided for indicating the operating condition preferably comprising a spike and the like which produces merely a small opening in the perforable surface. By comparison the opener means assigned to the active substance container consists of a relatively large-surface opener means to permit producing large or large-surface openings, thus permitting the active substance to quickly emerge from the container(s) once opened, due to the active substance being able to emerge from larger outlet openings.

In accordance with a further embodiment a trough-shaped container for receiving the active substance fluid emerging from the container is provided.

In one preferred embodiment of the evaporator device the mounting member is made as an absorbent member, for example of cellulose which extends into the trough-shaped container so that the active substance comes into intensive contact with the absorbent member to ensure evaporation of the full surface of the the absorbent member, i.e. thereby providing a relatively large surface for evaporation.

The active substance container(s) of the evaporator device are preferably not evident from the outside, while the container for indicating the operating status can be inspected via an opening from the outside of the housing. As the indicator fluid, a mixture of water and alcohol tinged by a coloring additive, for instance, can be employed. Following perforation of this indicator fluid container, its contents evaporate gradually, the composition of the indicator fluid being selected so that it evaporates over a time period within which the active substance fluid also evaporates completely. An empty indicator fluid container thus indicates that a new container filled with the active substance must be inserted.

Changing the active substance container and the indicator fluid container is easily done in conjunction with the evaporator device by removing the mounting member together with the empty containers from the housing and replacing them by a new mounting member with the containers filled. After hinging the housing sections together the containers are opened and/or perforated as required and thus placed in operation.

Evaporator devices of this kind are thus not suitable for allowing a relatively large quantity of active substances to be evaporated, to remedy, for example, a major odor problem. The invention creates an evaporator device which is capable of effectively eliminating major odor problems, whereby the active substance emerges after opening of the perforable surface of the active substance container in a relatively short period of time so that the corresponding container is depleted practically immediately or in a single action. With the aid of a separate indicator means the user is able to establish whether the evaporator device has effectively functioned or not.

BRIEF DESCRIPTION OF THE DRAWINGS

Preferred embodiments of the invention will now be described in the following with reference to the drawings to explain further features and advantages, wherein FIG. 3 is a plan view of the mounting member disposed between the housing sections, FIG. 4a, is a plan view of the means for indicating the operating condition, FIG. 4b is a side section view of the means according to FIG. 4a FIG. 5 is a section perspective view of an active substance container.

DESCRIPTION OF PREFERRED EMBODIMENTS

Figure 1:
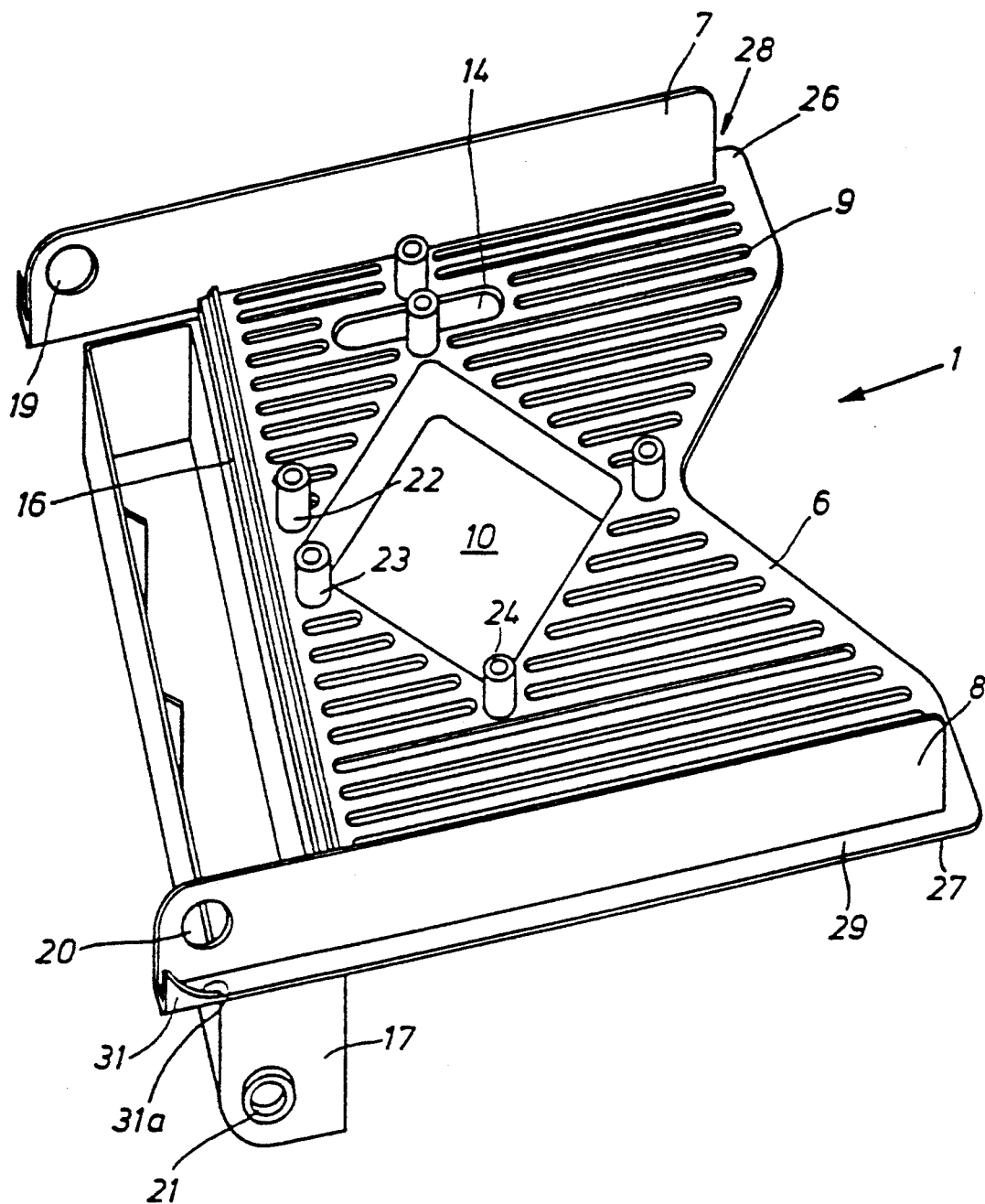
FIG. 1 is a perspective view of a first housing section of the evaporator device having a section to receive the active substance container and an opening through which the means for indicating the operating condition is visible.
Figure 2:
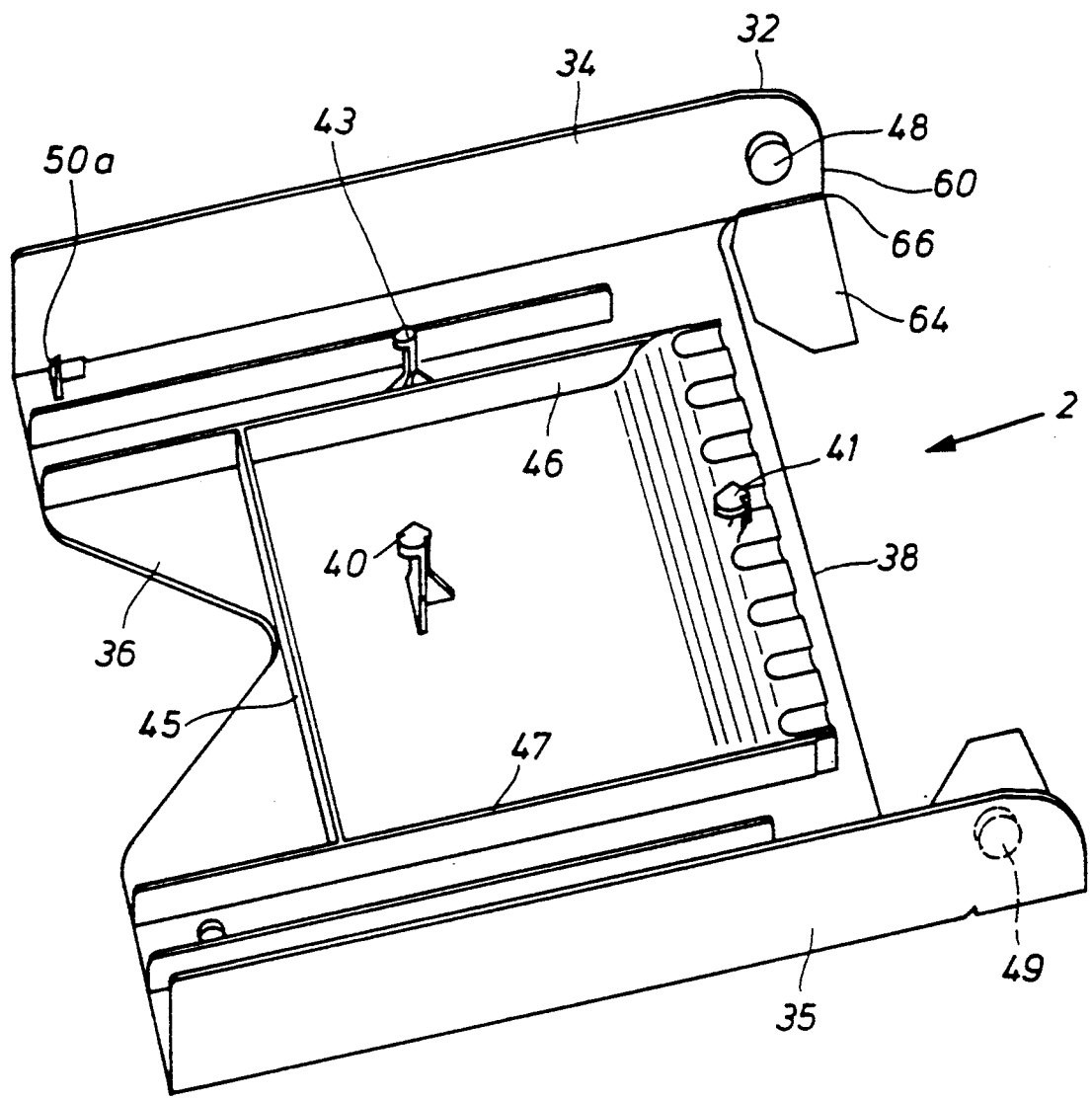
FIG. 2 shows the other housing section assigned to the housing section according to FIG. 1.

The following now explains a preferred embodiment of an evaporator device with reference to FIGS. 1 and 2. The housing of the evaporator device comprises two housing sections 1 and 2 which are locked to each other by means which will be described later, to produce a housing unit. Between the two housing sections 1 and 2 a mounting member is inserted as shown in FIG. 3 and identified by 3.

According to the embodiment as shown in FIG. 1 the housing section 1 comprises a housing wall 6 to which side webs 7, 8 are molded preferably vertically. In this embodiment the housing wall 6 features a plurality of slots or apertures 9 permitting evaporation of the active substances from the housing outwards. In addition a receiving section 10 is provided in the housing wall 6 to receive a suitably formed container containing the active substance fluid. The receiving section 10 defines a recess extending outwards in the housing wall 6, it resulting in a cover for the active substance container due to the floor identified by 12 in FIG. 6. The housing wall 6 further features an opening 14. This opening 14 is preferably slotted in shape, is vertically disposed and serves to permit inspection from outside of the means for indicating the operating condition of the device located behind this opening 14.

Figure 6:
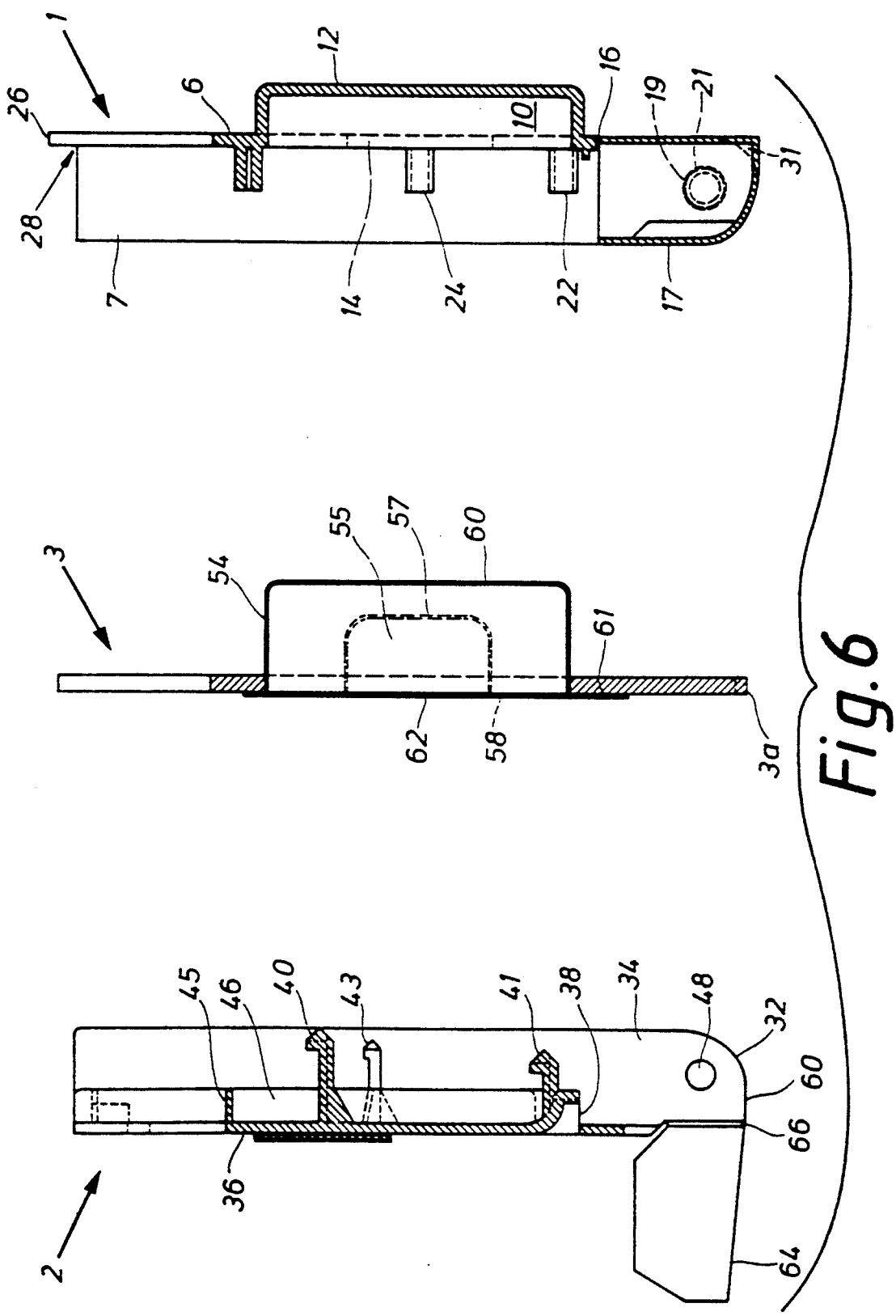
FIG. 6 is a schematic representation of the salient parts of the evaporator device to illustrate their interrelation.

In the embodiment shown a film hinge 16 is defined at the lower end of the housing wall 6. Via this film hinge 16 a trough-shaped body 17 is hinged to the housing wall 6. As shown in FIG. 1 the trough-shaped body 17 projects more or less perpendicular downwards from the housing wall. It is in this state that the part shown in FIG. 1 is molded. After molding in which also the trough-shaped body 17 is produced, this body 17 is turned clockwise about the film hinge 16 as shown in FIG. 1 upwards until it is located parallel to the two webs 7,8 (FIG. 6). Via means to be described later the body 17 is fixed or locked with respect to the webs 7,8.

In the embodiment as described in conjunction with FIG. 1 both webs 7, 8 are provided at their lower end with preferably circular openings 19, 20 which locate projections 21 which are formed preferably circular and protrude from the side of the trough-shaped body 17 when the body 17 has been hinged clockwise about the film hinge 16 from the position as shown in FIG. 1 into the position as shown in FIG. 6. The operating position of the trough 17 is evident from FIG. 6.

According to FIG. 1 pins 22, 23, 24 etc. and the like protruding from the housing wall 6 inwards in the housing serve to maintain the spacing of the mounting member 3 when inserted in housing section 1 with respect to the housing wall 6 the same as the height of the pins 22, 23, 24 etc.

The housing section 1 shown in FIG. 1 is defined so that the webs 7, 8 are displaced inwards with respect to the side edge 26, 27 of the housing wall 6, this in turn defining an edge or flange 28, 29 between the edge 26 or 27 and the web 7 or 8 which serves as the web, i.e. contact surface of the second housing section 2. The webs 7,8 protrude downwards from the housing wall 6 in FIG. 1 past the film hinge 16, but have an overall length corresponding to the length of the housing wall 6 plus the height of the trough-shaped body 17.

At the lower end of the flange or edge 28, 29 (FIG. 1) means are provided serving to limit the hinging capacity of the second housing section 2 with respect to the first housing section 1. These means are preferably defined as a pointed nose 31 the path of movement of which describes a section of an arc by its edge surface 31a facing upwards as shown in FIG. 1, this section of an arc more or less corresponding to the radius of curvature of the web of housing section 2 coming into contact with this path of movement. This edge is identified by 32 in FIG. 2 and is provided on each web 34, 35 of the housing section 2. The housing section 2 as shown in FIG. 2 also features a housing wall 36 substantially located between the two webs 34, 35. On the housing wall 36 a lower front edge 38 is defined, past which the webs 34, 35 project. The two housing sections 1, 2 have, for example, the same height and roughly the same width and are made of plastic.

The housing section 2 according to FIG. 2 is provided with opener means, a first opener being defined as pointed spikes 40, 41 molded to the housing wall 36, while a second opener is defined as a single spike 43. Opener 40, 41 is formed on the housing wall 36 at a position which is roughly opposite to the position of the receiving section 10, while the opener 43 protrudes from the housing wall 36 at a position opposite the opening 14 of the housing section 1. To ensure a controlled flow of indicator fluid from the container (described later) the housing wall 36 is provided with vertically projecting fins 45, 46, 47. The fins 46, 47 are oriented in the vertical direction; fin 45 is located perpendicular to and above the fins 46, 47.

The tip or shape of the spike-like members 40, 41, 43 is selected differingly to permit more or less pronounced perforation of the perforable container surfaces.

On the right-hand lower side of the webs 34, 35 as shown in FIG. 2 pins 48, 49 are provided which project inwards and are preferably circular in shape, the dimensions of which are selected so that they can engage in the openings defined in the latching projections 21.

To assemble the two housing sections 1 and 2, as shown in FIGS. 1 and 2, together, the trough-shaped body 17, as already described, is first hinged clockwise from its position as shown in FIG. 1 about the film hinge 16 until the latching projections 21 engage in the openings 19, 20 so that the body 17 is located practically parallel to the webs 7, 8. The housing section 2 is then inserted in housing section 1 so that the pins 48, 49 engage from the outside the openings or recesses (which are merely suggested in FIG. 1) formed in the latching projections 21. The webs 34, 35 are disposed outwardly to one side of the webs 7, 8 and take hold of the webs 7, 8 when the two housing sections 1, 2 are moved towards each other about their common hinge axis. The hinge axis is defined by the parts 19, 20, 48, 49. Following assembly of the two housing sections 1 and 2 the mounting member 3 can be inserted as is explained in the following.

In the vicinity of the upper front edge of, for example, housing section 2, latching members 50a, are provided which are made to engage the webs 7, 8 of housing section 1, thereby holding the two housing sections 1, 2 together in a parallel location.

In the embodiment of FIGS. 1 and 2 the mounting member 3 (shown in FIG. 3) is formed in such a way that it substantially contains two openings or apertures 51, 52. The more or less rectangular mounting member 3 features the one opening 51 in a position which is more or less in alignment with the receiving section 10, after the mounting member 3 has been inserted, while the opening 52 is positioned more or less opposite the opening 14 of housing section 1. Openers 40, 41 and 43 respectively are formed suitably assigned on housing section 2, i.e. openers 40, 41 in the form of spikes 40, 41 are directed at the opening 51 of the mounting member 3, while the spike 43 is directed at the opening 52 of the mounting member 3 inserted in the housing. The mounting member 3 (FIG. 3) serves to receive at least two containers which will now be described with reference to FIGS. 4 and 5.

Containers 54 and 55 as shown in FIG. 5, and FIGS. 4a and 4b respectively are inserted in the openings 51 and 52 respectively of the mounting member 3. Container 55 will first be described. Container 55 serves as a means of indicating the operating condition, i.e. it can be of any, preferably elongated, shape and comprises a molded plastic component or a dish-shaped part 57 of plastic which is transparent by nature. The opening of this part 57 is closed off by a perforable film or foil 58 and the like after filling with a fluid which is preferably a mixture of water and alcohol with a coloring agent and designed to slowly emerge or evaporate from the container 55 once the film or foil 58 has been perforated. The opening 52 in the mounting member 3 has almost precisely the same shape as the container part 57 and is preferably shaped as a vertical slot. As shown by FIG. 4b a flange 59 is formed on the container part 57. This flange 59 serves to seal-mount the perforable film or foil 58. The container 54 as shown in FIG. 5 has practically the same configuration at that of container 55 but has preferably a container body 60 which is rectangular or square in shape, formed with a circumferential flange 61 projecting outwards and serving to secure a perforable film or foil 62. The opening 51 in the mounting member 3 has the same shape as the container body 60. Accordingly, containers 55 and 54 can be inserted in the mounting member 3, the corresponding flange sections 59 and 61 coming into contact with the outer surface on the one side of the mounting member 3 while the container body 57 and 60 respectively protrudes from the corresponding opening 52 and 51 respectively on the other side of the mounting member 3. By this arrangement the two containers 54, 55 are held on and in the mounting member 3 respectively, the mounting member 3 positioning them opposite the opener means, on the one hand, and opposite the opening 52 and 51 respectively, on the other.

FIG. 6 shows a side sectional view of each of the three substantial components 1, 2 and 3 of the evaporator device. From FIG. 6 it is evident that the mounting member 3 has a height substantially corresponding to that of the housing sections 1 and 2. Together with the containers 54, 55 the mounting element 3 is inserted in the housing section 1 so that the lower edge 3a of the mounting member 3 is located within the trough-shaped body 17. After hinging the housing sections 1 and 2 together each container 54 and 55 is automatically opened or perforated by the corresponding spikes 40, 41 and 43 respectively, so that the fluid is able to flow from the container 54 downwards into the trough 17. The active substance fluid is absorbed by the mounting member 3 which is preferably made of cellulose, the mounting member 3 thus defining an evaporation surface corresponding to the entire surface of the mounting member 3.

As is evident from FIG. 6, after the housing sections 1 and 2 have been assembled and hinged together about the axis of housing section 2 as determined by the hinge pins 48, the spikes 40, 41 and 43 are moved in the direction of the containers 54, 55. In the course of the hinged movement of, for example, housing section 2 about the axis defined by the hinge pins 48 in the direction of the housing section 1, the spikes 40 through 43 puncture the assigned perforable films or foils 62, 58, this ensuring, on the one hand, depletion of container 54 and, on the other, Perforation of film or foil 58 to the prescribed degree. The evaporator device is automatically started by hinging the two housing sections 1 and 2 together.

The size of the container 55 and the nature of the mixture contained therein are selected so that after some time the contents of the container have evaporated, this corresponding to the normal or average operating time of the evaporator described. Accordingly the user of the evaporator device is thus able to recognize simply by inspecting the container 55, i.e. the liquid level contained therein, whether the evaporator device is still effective or how long it will continue to be effective. When the container 55 is fully depleted the user will recognize that the mounting member 3 together with its containers 55, 54 need to be replaced by new such means.

Replacing the mounting member 3 is easily done by opening the two housing sections 1, 2 in the direction opposite to that described above, i.e. by hinging them apart about the axis determined by the parts 48, 49, 19, 20, 21. For this purpose, the upper edges of the two housing sections 1,2 are pulled in opposing directions to each other. After opening the housing the mounting plate 3 can be removed. The containers 54, 55 contained therein are preferably latched in place in the mounting plate 3. The mounting plate 3 is then replaced by a new mounting plate having fully charged containers 54, 55 so that its lower edge 3a is inserted to locate within the trough-shaped body 17 downwards in the housing sections 1, 2 and both container bodies 57, 60 face in the direction of housing section 1.

As evident from the drawings in FIG. 6 one preferred embodiment provides for a restricted opening angle between the housing sections 1 and 2 by housing section 1 featuring a nose-shaped projection 31 which acts together with the lower part of the web 34, 35 or a curved surface 32 thereof extending vertical to the housing wall 36. As shown in FIGS. 2 and 6 the path 32 described by the webs 34, 35 is curved so that in the direction of the housing wall 36 it transfers to a section 60 disposed perpendicular to the housing wall 36. As soon as this more or less straight edge section 60 comes into contact with the edge 31a so that guide edges having differing radii of curvature face each other, a latching action is produced between the housing sections 1, 2 which counteracts any further opening movement between the two housing sections 1,2. Accordingly, any further movement of the housing section 2 away from housing section 1 about the hinge axis is blocked, as long as the forces exerted on the two housing sections 1,2 is not too high to pull the latter apart.

In accordance with yet a further embodiment of the evaporator device the housing section 2 is designed so that on the lower part of the webs 34, 35 projecting from the housing wall 36 feet 64 are formed in a manner as indicated in FIG. 6 which are hinged by film hinges 66 on the housing section 2 formed parallel to and preferably in the plane of the housing wall 36. Accordingly the feet 64 can be disposed in the position as shown in FIG. 6, i.e. at right angles to the housing wall 36 so that the complete housing can be stood on a flat surface, or they can be hinged into the plane of the housing wall 36 so that a housing comprising sections 1 and 2 can be secured or bonded to a wall, the rear side of housing section 2 then being in contact with the wall.

The embodiment of the evaporator device described above features a single container 54 to receive the active substance. Instead of a single container, two or more such containers may be used together with a corresponding additional number of receiving sections 10 on the part of the housing section 1 and opener means on housing section 2.

Yet a further embodiment of the invention provides for each receiving section 10 to feature a preferably vertical slot to allow inspection, at least in part, of the active substance container 54 located behind the slot to see whether the container 54 is depleted or not once the two housing sections 1 and 2 have been assembled into the operating position. By means of this slot (not shown in the drawing) it can also be established from the outside, whether a container 54 exists in the housing at all. In the embodiment as described with reference to FIGS. 1 through 6 the container 54 is, on the contrary, completely concealed by the housing wall 6, while the container 55 and its indicator fluid is arranged flat behind the opening 14 so that it can be seen from the outside.

The evaporator device according to the invention features a housing preferably comprising only two housing halves for facilitated assembly, each housing half being of simple configuration and permitting low-cost manufacture. The opener function required of the spikes 40, 41 and 43 can be achieved by employing spikes of differing length. In the embodiment shown, the spikes 40, 41 for opening the container 54 are extra long to open the container 54 so thoroughly that complete depletion of the active substance into the trough formed by the body 17 is quickly ensured. By contrast, the spike 43 is shorter in length and sharper pointed to perforate the container 55 only slightly, thus ensuring slow evaporation of the fluid contained therein, contrary to a sudden or fast depletion. It is obvious that the size of the container 55 and the nature of the fluid contained therein are adapted accordingly so that the fluid contained therein evaporates with a time period during which the active substance leaving the container 54 is typically fully depleted or evaporated.

What is claimed:

1. An evaporator device for a volatile active substance having a housing containing ports through which the active substance can emerge to the surroundings, said housing comprising:
   at least two housing sections which are movable about a hinge axis,
   at least one receiving section for a container for the active substance, defined in one of said at least two housing sections, having at least one opener means arranged on one of said at least two housing sections for opening said container,
   means for indicating the operating condition of said device,
   said indicating means comprising a container holding an indicator fluid, said indicator fluid container being opened when said evaporator device is used, so that the said indicator fluid is able to evaporate, whereby the evaporation of said indicator fluid is continued over a time period in which said active substance is depleted,
   a mounting member for mounting said indicator fluid container between said at least two housing sections,
   one of said housing sections incorporating an opening behind which said indicator fluid container is mounted so that it can be viewed from outside the housing to recognize said operating condition while said container for said active substance cannot be viewed from the outside.

2. A device as set forth in claim 1, wherein said mounting member further mounts said active substance container.

3. A device as set forth in claim 1, wherein said mounting member includes at least two openings in which said active substance container and said indicator fluid container can be inserted.

4. A device according to claim 1, wherein said mounting member is adapted to absorb the active substance of said active substance container,
   said mounting member having a height being essentially the same as a height of said at least two housing sections,
   wherein said mounting member is defining as evaporation surface.

5. An evaporator device for a volatile active substance having a housing containing ports through which the active substance can emerge to the surroundings, said housing comprising:
   at least two housing sections which are movable about a hinge axis,
   at least one receiving section for a container for the active substance, defined in one of said at least two housing sections, having at least one opener means arranged on one of said at least two housing sections for opening said container,
   means for indicating the operating condition of said device,
   said indicating means comprising a container holding an indicator fluid, said indicator fluid container being opened when said evaporator device is used, so that the said indicator fluid is able to evaporate, whereby the evaporation of said indicator fluid is continued over a time period in which said active substance is depleted,
   a mounting member for mounting said indicator fluid container between said at least two housing sections,
   one of said housing sections incorporating an opening behind which said indicator fluid container is mounted so that it can be viewed from outside the housing to recognize said operating condition while said container for said active substance cannot be viewed from the outside,
   said mounting member comprising at least two openings in which said active substance container and said indicator fluid container can be inserted, said openings of said mounting member being shaped and sized so that said active substance container and said indicator fluid container are clamped in said openings of said mounting member.

6. An evaporator device for a volatile active substance having a housing containing ports through which the active substance can emerge to the surroundings, said housing comprising:
   at least two housing sections which are movable about a hinge axis, at least one receiving section for a container for the active substance, defined in one of said at least two housing sections, having at least one opener means arranged on one of said at least two housing sections for opening said container, means for indicating the operating condition of said device, said indicating means comprising a container holding an indicator fluid, said indicator fluid container being opened by said at least one opener means when said evaporator device is used, so that the said indicator fluid is able to evaporate, whereby the evaporation of said indicator fluid is continued over a time period in which said active substance is depleted, a mounting member for mounting said indicator fluid container between said at least two housing sections, one of said housing sections incorporating an opening behind which said indicator fluid container is mounted so that it can be viewed from outside the housing to recognize said operating condition while said container for said active substance cannot be viewed from the outside, said active substance container and said indicator fluid container each comprising a planar layer which is perforable by said at least one opener means and a circumferential collar to which said perforable layer is secured fluid-tight, said mounting member having first and second sides and at least one opening in which one of said active substance container and said indicator fluid container is inserted so that said circumferential collar comes to rest on said first side and said container extends past said second side of said mounting member.

7. A device as set forth in claim 6, wherein one of said housing sections comprises a trough-shaped body.

8. An evaporator device for a volatile active substance having a housing containing ports through which the active substance can emerge to the surroundings, said housing comprising:

at least two housing sections which are movable about a hinge axis, at least one receiving section for a container for the active substance, defined in one of said at least two housing sections, having at least one opener means arranged on one of said at least two housing sections for opening said container, means for indicating the operating condition of said device, said indicating means comprising a container holding an indicator fluid, said indicator fluid container being opened by said at least one opener means when said evaporator device is used, so that the said indicator fluid is able to evaporate, whereby the evaporation of said indicator fluid is continued over a time period in which said active substance is depleted, a mounting member for mounting said indicator fluid container between said at least two housing sections, one of said housing sections incorporating an opening behind which said indicator fluid container is mounted so that it can be viewed from outside the housing to recognize said operating condition while said container for said active substance cannot be viewed from the outside, said active substance container and said indicator fluid container each comprising a planar layer which is perforable by said at least one opener means and a circumferential collar to which said perforable layer is secured fluid-tight.

9. An evaporator device for a volatile active substance having a housing containing ports through which the active substance can emerge to the surroundings, said housing comprising:

at least two housing sections which are movable about a hinge axis, at least one receiving section for a container for the active substance, defined in one of said at least two housing sections, having at least one opener means arranged on one of said at least two housing sections for opening said container, means for indicating the operating condition of said device, said indicating means comprising a container holding an indicator fluid, said indicator fluid container being opened when said evaporator device is used, so that the said indicator fluid is able to evaporate, whereby the evaporation of said indicator fluid is continued over a time period in which said active substance is depleted, a mounting member for mounting said indicator fluid container between said at least two housing sections, one of said housing sections incorporating an opening behind which said indicator fluid container is mounted so that it can be viewed from outside the housing to recognize said operating condition while said container for said active substance cannot be viewed from the outside, one of said housing sections comprising a trough-shaped body provided to receive and allow evaporation of said active substance flowing from said active substance container after its opening by said at least one opener means, and a film hinge hingeably connecting said trough-shaped body to said housing section comprising said trough-shaped body.

10. An evaporator device for a volatile active substance having a housing containing ports through which the active substance can emerge to the surroundings, said housing comprising:

at least two housing sections which are movable about a hinge axis, at least one receiving section for a container for the active substance, defined in one of said at least two housing sections, having at least one opener means arranged on one of said at least two housing sections for opening said container, means for indicating the operating condition of said device, said indicating means comprising a container holding an indicator fluid, said indication fluid container being opened when said evaporator device is used, so that the said indicator fluid is able to evaporate, whereby the evaporation of said indicator fluid is continued over a time period in which said active substance is depleted, a mounting member for mounting said indicator fluid container between said at least two housing sections, one of said housing sections incorporating an opening behind which said indicator fluid container is mounted so that it can be viewed from outside the housing to recognize said operating condition while said container for said active substance cannot be viewed from the outside, one of said housing sections comprising a trough-shaped body provided to receive and allow evaporation of said active substance flowing from said active substance container after its opening by said it least one opener means, a film hinge hingeably connecting said trough-shaped body to said housing section comprising said trough-shaped body, and said housing section comprising said trough-shaped body further comprising protruding webs.

11. An evaporator device for a volatile active substance having a housing containing ports through which the active substance can emerge to the surroundings, said housing comprising:

at least two housing sections which are movable about a hinge axis, at least one receiving section for a container for the active substance, defined in one of said at least two housing sections, having at least one opener means arranged on one of said at least two housing sections for opening said container, means for indicating the operating condition of said device, said indicating means comprising a containing holding an indicator fluid, said indication fluid container being opened when said evaporator device is used, so that the said indicator fluid is able to evaporate, whereby the evaporation of said indicator fluid is continued over a time period in which said active substance is depleted, a mounting member for mounting said indicator fluid container between said at least two housing sections, one of said housing sections incorporating an opening behind which said indicator fluid container is mounted so that it can be viewed from outside the housing to recognize said operating condition while said container for said active substance cannot be viewed from the outside, one of said housing sections comprising a trough-shaped body provided to receive and allow evaporation of said active substance flowing from said active substance container after its opening by said at least and opener means, a film hinge hingeably connecting said trough-shaped body to said housing section comprising said trough-shaped body, and said housing section comprising said trough-shaped body further comprising protruding webs each including openings, and wherein said trough-shaped body comprises projections adapted to detent in said openings of said protruding webs.

12. An evaporator device for a volatile active substance having a housing containing ports through which the active substance can emerge to the surroundings, said housing comprising:

at least two housing sections which are movable about a hinge axis, at least one receiving section for a container for the active substance, defined in one of said at least two housing sections, having at least one opener means arranged on one of said at least two housing sections for opening said container, means for indicating the operating condition of said device, said indicating means comprising a container holding an indicator fluid, said indicator fluid container being opened when said evaporator device is used, so that the said indicator fluid is able to evaporate, whereby the evaporation of said indicator fluid is continued over a time period in which said active substance is depleted, a mounting member for mounting said indicator fluid container between said at least two housing sections, one of said housing sections incorporating an opening behind which said indicator fluid container is mounted so that it can be viewed from outside the housing to recognize said operating condition while said container for said active substance cannot be viewed from the outside, one of said housing sections comprising a trough-shaped body provided to receive and allow evaporation of said active substance flowing from said active substance container after its opening by said at least one opener means, a film hinge hingeably connecting said trough-shaped body to said housing section comprising said trough-shaped body, said housing section comprising said trough-shaped body further comprising protruding webs each including openings, said trough-shaped body comprising projections adapted to detent in said openings of said protruding webs, wherein said at least one receiving section for said active substance container is provided in said housing section comprising said trough-shaped body.

13. An evaporator device for a volatile active substance having a housing containing ports through which the active substance can emerge to the surroundings, said housing comprising:

at least two housing sections which are movable about a hinge axis, at least one receiving section for a container for the active substance, defined in one of said at least two housing sections, having at least one opener means arranged on one of said at least two housing sections for opening said container, means for indicating the operating condition of said device, said indicating means comprising a container holding an indicator fluid, said indicator fluid container being opened when said evaporator device is used, so that the said indicator fluid is able to evaporate, whereby the evaporation of said indicator fluid is continued over a time period in which said active substance is depleted, a mounting member for mounting said indicator fluid container between said at least two housing sections, one of said housing sections incorporating an opening behind which said indicator fluid container is mounted so that it can be viewed from outside the housing to recognize said operating condition while said container for said active substance cannot be viewed from the outside, one of said housing sections comprising a trough-shaped body provided to receive and allow evaporation of said active substance flowing from said active substance container after its opening by said at least one opener means;

a film hinge hingeably connecting said trough-shaped body to said housing section comprising said trough-shaped body, said housing section comprising said trough-shaped body further comprising protruding webs each including openings, said trough-shaped body comprising projections adapted to detent in said openings of said protruding webs, said projections defining connecting members arranged to receive pins provided on the other of said at least two housing sections.

14. A device as set forth in claim 13, including means for limiting the relative movement of said at least two housing sections.

15. A device as set forth in claim 13, wherein said webs comprise vertically projecting webs.

16. An evaporator device for a volatile active substance having a housing containing ports through which the active substance can emerge to the surroundings, said housing comprising:

at least two housing sections which are movable about a hinge axis, at least one receiving section for a container for said volatile substance, defined in one of said at least two housing sections, at least one opener means arranged on one of said at least two housing sections for opening said container, means for indicating the operating condition of said device, said indicating means comprising a container for an indicator fluid, said indicator fluid container being opened when said evaporator device is used, so that said indicator fluid is able to evaporate, whereby the evaporation of said indicator fluid is continued over a time period in which said active substance is depleted, a mounting member for mounting said indicator fluid container between said at least two housing sections, one of said housing sections comprising an opening behind which said indicator fluid container is mounted so that it can be viewed from outside the said housing to recognize said operating condition while said active agent container cannot be viewed from the outside, and wherein said at least one opener means is formed by at least one spike.

17. An evaporator device for a volatile active substance having a housing containing ports through which the active substance can emerge to the surroundings, said housing comprising:

at least two housing sections which are movable about a hinge axis, at least one receiving section for a container for said volatile substance, defined in one of said at least two housing sections, at least one opener means formed by at least one spike and arranged on one of said at least two housing sections for opening said container, means for indicating the operating condition of said device, said indicating means comprising a container for an indicator fluid, said indicator fluid container being opened when said evaporator device is used, so that said indicator fluid is able to evaporate, whereby the evaporation of said indicator fluid is continued over a time period in which said active substance is depleted, a mounting member for mounting said indicator fluid container between said at least two housing sections, one of said housing sections comprising an opening behind which said indicator fluid container is mounted so that it can be viewed from outside the said housing to recognize said operating condition while said active agent container cannot be viewed from the outside, each of said housing sections comprising vertically projecting webs, and folding feet on a lower part of said webs of one of the said at least two housing sections for adjusting the feet vertically relative to said housing to enable said housing to be placed on a planar surface.

* * * * *